United States Patent [19]

Mennen

[11] 4,364,382

[45] Dec. 21, 1982

[54] INTERNAL FIXATION DEVICE FOR BONE FRACTURES

[76] Inventor: Ulrich Mennen, 49 Hill Ter., Riviera, Pretoria, Transvaal, South Africa

[21] Appl. No.: 179,521

[22] Filed: Aug. 19, 1980

[30] Foreign Application Priority Data

Aug. 23, 1979 [ZA] South Africa ............... 79/0862
Jan. 21, 1980 [ZA] South Africa ............... 80/0327

[51] Int. Cl.$^3$ ............................... A61F 5/04
[52] U.S. Cl. ................... 128/92 D; 128/92 B
[58] Field of Search .......... 128/92 D, 92 B, 92 G, 128/92 BC

[56] References Cited

U.S. PATENT DOCUMENTS

| 583,455 | 6/1897 | Bush | 128/92 D |
|---|---|---|---|
| 3,593,709 | 7/1971 | Halloran | 128/92 D |
| 3,893,196 | 7/1975 | Hochman | 128/92 BC |
| 3,955,567 | 5/1976 | Richmond et al. | 128/92 D |
| 3,960,147 | 6/1976 | Murray | 128/92 B |
| 4,047,524 | 9/1977 | Hall | 128/92 D |
| 4,261,350 | 4/1981 | Branemark et al. | 128/92 BC |
| 4,261,351 | 4/1981 | Scherfel | 128/92 BC |
| 4,269,180 | 5/1981 | Dall et al. | 128/92 D |

FOREIGN PATENT DOCUMENTS

| 2211851 | 7/1974 | France | 128/92 B |
|---|---|---|---|
| 2353274 | 12/1977 | France | 128/92 B |
| 632351 | 11/1978 | U.S.S.R. | 128/92 D |

Primary Examiner—Kyle L. Howell
Assistant Examiner—C. W. Shedd
Attorney, Agent, or Firm—Fred Wiviott

[57] ABSTRACT

This invention provides an internal fixation device for a bone fracture, the device comprising a metallic plate having edge fastening formations formed on at least two edges of the plate which is adapted to be secured to a bone fracture site by deforming the plate and engaging the fastening formations directly to the bone by penetration into the bone, thereby bridging a bone fracture.

3 Claims, 2 Drawing Figures

4,364,382

INTERNAL FIXATION DEVICE FOR BONE FRACTURES

FIELD OF THE INVENTION

This invention relates to an internal fixation device for bone fractures.

DESCRIPTION OF THE PRIOR ART

Although bone fractures have been fixed with the help of metal plates using screws to fix each plate, such plates have various attendant problems.

In the first instance, a drill, bits and screws are required. Secondly, a certain amount of damage is occasioned to fractured bones during the drilling operation. Thirdly, a considerable amount of soft tissue dissection is required for purposes of access. Fourthly, support of the fractured zone is borne only by the portion of the plate between the central screws. In addition, such plates lend stability to a fractured bone only in one plane. Fifthly, on account of the intimate plate/bone contact, incorporation or bone overgrowth tends to take place, and because of the nature of these plates, tissues/bone contact is completely excluded by these plates.

SUMMARY OF THE INVENTION

It is an object of the present invention to provide an internal fixation device which overcomes, at least partly, the above disadvantages, especially when used according to the knowledge and experience of the inventor.

According to the invention there is provided an internal fixation device for a bone fracture, the device comprising a metallic plate having edge fastening formations formed on at least two edges of the plate which is adapted to be secured to a bone fracture site by deforming the place and engaging the fastening formations directly to the bone by penetration into the bone thereby bridging a bone fracture.

The plate may have an elongate shape in plan view, the edge fastening formation being formed at least along the two longer edges of the plate.

The plate may be provided in an axially symmetrical channel-like form having the fastening formations faced inwardly.

The plate may preferably have a stiffening formation provided axially on the plate, and in the case of the plate being provided in a channel-like form the stiffening formation will be provided along the central ridge of the plate.

The plate may have an axially located opening near at least one end of the plate and preferably near each end of the plate.

In a preferred form of the invention, the plate may be made of stainless steel, or any other suitable metal or alloy.

In a further preferred embodiment, the plate may have a fern-like shape in plan view, having a plurality of finger members along at least two sides of the plate, each finger member having an edge fastening formation at the extremity thereof.

Each fastening formation may preferably be a pointed or sharpened edge or extremity of a finger member, as the case may be. More preferably, each fastening formation may extend perpendicularly from the edge or finger member as the case may be.

The plate may be adapted to be secured to a bone fracture site by crimping the plate about the fractured bone to engage the fastening formations to the bone about the fractured site.

The plate may be of a size to extend at least half-way about the circumference of a bone when the bone is tubular in cross section.

The plate may be adapted so that its ridge is spaced from the bone when the plate is secured to the fractured site.

The fixation device as hereinbefore described may be provided in a combination with a pincer-like securing tool each jaw member thereof having a concave formation, the tool being adapted to deform the plate by way of the concave formations thereby to engage the fastening formations to the bone at the fracture site.

The fixation device may also be provided in combination with an expander tool adapted for forcing apart opposite fastening formations of the plate.

The fixation device may additionally be provided in combination with a compression tool having three engaging members, one engaging member being adapted to secure an end or an opening of the plate and the other two engaging members being adapted to engage a bone and to compress a fractured bone during securing of the plate to a bone fracture site.

Further according to the invention, there is provided a kit comprising at least one internal fixation device as hereinbefore described, in combination with at least one securing tool, at least one expanding tool, at least one compression tool, the aforementioned tools being as hereinbefore described, for holding the plate on the bone, for example, a bone-holding clamp, such as a Verbrugge-type clamp, and a removing tool as hereinbefore described.

Yet further according to the invention there is provided a fixation device as hereinbefore described, whenever used to assist in achieving healing of a bone fracture.

BRIEF DESCRIPTION OF THE DRAWINGS

The invention will now be described by way of example, with reference to the following drawings, in which.

DESCRIPTION OF THE PREFERRED EMBODIMENT

Figure 1:
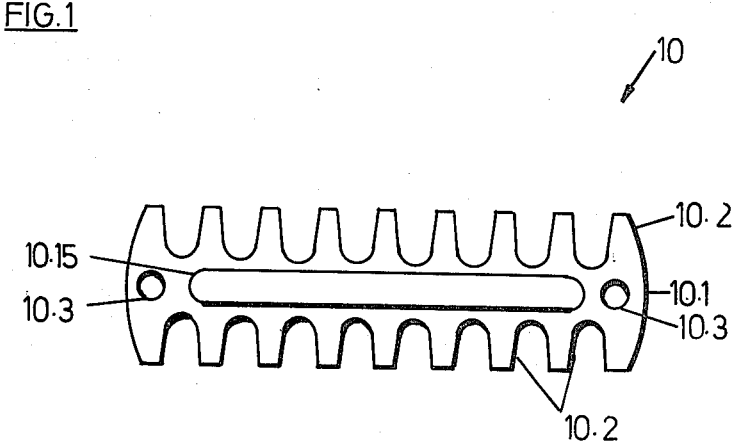
FIG. 1 shows a plan view of an internal fixation device for a bone fracture, in accordance with the invention.

Unless otherwise indicated, like reference numerals refer to like parts in the drawings.

Referring to the drawings, reference numeral 10 refers generally to an internal fixation device according to the invention made of surgical stainless steel having a thickness of approximately one milimeter. The device 10 is in the form of a tunnel-like plate having a fern-like appearance in plan view (FIG. 1).

The device or plate 10 has a ridge or spine portion 10.1. having a raised deformed stiffening formation 10.15 to provide additional rigidity in the plate 10. The plate 10 also has a plurality of finger members 10.2. extended along each of its longer edges. The extremity of each finger member 10.2. is bent inwardly to provide a sharpened fastening formation 10.25 pointing inwardly, the (internal) angle between the fastening formation 10.25 and the inside surface of each finger member 10.2 being 90°.

An opening 10.3 is provided in the ridge 10.1 of the plate 10 near each end thereof.

Figure 2:
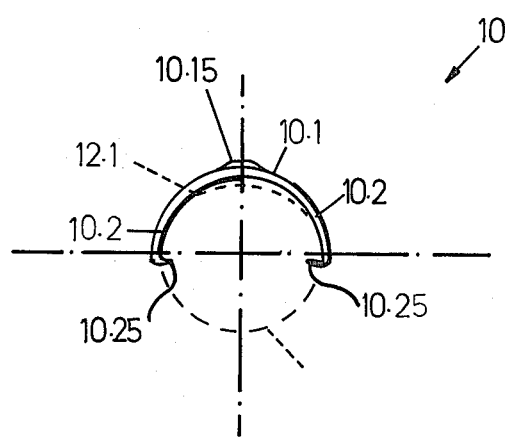
FIG. 2 shows an end view of the fixation device of FIG. 1 when crimped to a tubular bone.

In use, the plate 10 is applied as follows. A plate of suitable dimensions (for example diameter and length) will be selected for each particular application. With reference to FIG. 2, a plate 10 has been selected with a diameter approximately equal to the diameter of the bone 12 showed in dotted lines. It may, however, be preferable to use a plate 10 having a diameter slightly larger than the diameter of the bone in order for the fastening formation 10.25 to engage the bone below its centre line (as shown in FIG. 2). The fastening formations may also, however, if desired, engage the bone at its centre line (not shown in FIG. 2) which also provides a satisfactory arrangement.

The plate 10 is then fitted over the bone 12 so as to bridge a fracture in the bone, and the plate 10 is positioned on the bone 12 as shown in FIG. 2.

A securing tool in the shape of a pincer or pliers (not shown) each jaw member thereof having a smooth concave formation on the interior surface of the jaws is then placed with the concave formation in contact with each side 10.2 of the plate 10. The pincer or pliers is then squeezed to engage and penetrate each opposite pair of fastening formations 10.25 in the bone 12. See FIG. 2. In the case that a finger formation or a pair of finger formations have to be forced apart, for example in the case of a part of the bone having a larger diameter, an expander tool as known in the medical or mechanical fields may be used for forcing apart opposite fastening formations 10.2 of the plate 10 prior to applying the securing tool as described above. The expander tool is also not shown.

The action of the pincer or pliers referred to earlier is to reduce the diameter of the plate 10 during engagement and penetration of the fastening formations 10.25 into the bone 12. This results in an "arching" of the ridge 10.1. of the plate 10 thereby spacing the ridge 10.1. away from the crown 12.1. of the bone 12.

In the case that the fractured bone requires compression, a compression tool (also not shown) may be used having three engaging members, one engaging member being adapted to engage one end or an opening 10.3. of the plate 10, and the other two engaging members being adapted to engage a bone (and possibly having suitable formations for gripping the bone), the compression tool then being adapted to draw the engaged bone towards the fracture site and towards the plate 10, thereby to compress the fractured bone during securing (or prior to final securing) of the plate 10 to the bone fracture site.

The invention may preferably be provided in a kit with at least one plate such as the plate 10, but preferably with a range of plates of various sizes for dealing with bones of different diameters and shapes, in combination with a securing tool, an expanding tool, and a compression tool, as described above.

A removing tool (also not shown) may be included in the kit in the case that removal of the plate 10 is desired from the bone 12. The removing tool is preferably in the form of a pair of narrow-nose pliers, each jaw member of which has sharp notch therein immediately of the end of the jaw member. The combined notch in the two jaw members enable a finger member 10.2. to be gripped in the combined notch and bent outwardly away from the bone 12. If required, a small bone clip may be removed from either side of tfhe finger member 10.2. to facilitate gripping of the finger member 10.2. by the combined notch of the removing tool, prior to bending outwardly to disengage and withdraw the fastening formation 10.25 from the bone 12.

The plate 10 essentially provide a new device and means for internal fixation of fractured bones without the help of screws, although, if desired and if required, a screw may be provided in each of the openings 10.3. in order further to secure the plate 10 to a fractured bone 12.

Fractures which can be treated with the present invention include radius and/or ulna fractures, humerus fractures, femur fractures, and under certain conditions metacarpal fractures.

Based on experimental work with the invention (especially on baboons), the inventor has found that the invention provides the following advantages:

(a) A very simple device and technique is provided for internal fixation of bone fracture.
(b) Operation time can be considerably reduced.
(c) No drilling machine, or screws are required.
(d) Minimal soft tissue dissection is required and reduction of blood supply to the fracture(s) is minimised.
(e) The plate is designed so that only in the immediate vicinity where each fastening formation 10.25 is inserted and penetrates into the bone, is periosteal circulation impaired, and the order hereof is of no practical import.
(f) Very simple equipment is required for the fixation i.e. only a securing tool, optionally an expander tool, and optionally a compression Tool (as described above).
(g) The plate, under certain circumstances, is ideal not only for simple fractures but also for comminuted fractures; child fractures; re-fractures; and non-knitting.
(h) Minimal bone damage is caused.
(i) Fracturing of the plate will not readily take place, since the plate transfers forces across two or more bone portions along its entire length.
(j) The plate is dimentionally stable in two planes as opposed to plates with screws which appear to be dimentionally stable in only one plane.
(k) Since the plate is provided above the periost and even above the ligament ends (on account of the ridge 10.1 of the Plate 10 being spaced above the bone crown 12.1), the problem associated with other plates i.e. incorporation or bone overgrowth apparently does not take place. The plate evidently is simply moved away from the bone, and therefore removal after bone repair has taken place, appears to be unnecessary.

Results in using the plate has shown the following:
(i) Minimal callus formation at fracture ends;
(ii) In some cases primary bone repair may occur;
(iii) No bone fractures have come apart.
(iv) Full stability and immobilisation is retained;
(v) No function reduction has been observed.

It is possible that under certain circumstances, no additional fixation for example such as plaster of Paris may be required postoperatively. Naturally, the scope of the invention is not limited to the embodiments herein described, and, for example, the plate 10 may be provided with more or fewer finger members 10.2 and the plate 10 may naturally be provided in any suitable size and shape, depending on any particular requirement.

Naturally, besides using the plate 10 for fixing fractures, the plate 10 may alternatively be used for osteotomies.

I claim:

1. An internal fixation device for bone fractures comprising a unitary metallic member including:

an elongated central portion having upper and lower surfaces which are respectively convex and concave;

a plurality of arcuate finger portions extending integrally from the opposite sides of said central portion and extending generally downwardly and outwardly from said central portion in an opposed relation to define a generally channel shaped structure; wherein said finger portions are generally arranged transverse to the longitude of said elongated central portion;

each finger portion terminating in an inwardly extending fastening means having a sharpened edge constructed and arranged for penetration into said bone;

said central portion having an elongated stiffening corrugation extending longitudinally for a majority of its length and being elevated from said upper surface, said central portion and said stiffening corrugation being constructed and arranged so that said device flexes at said stiffening formation; whereby, when said member is deformed by forcing said finger portions toward each other inwardly for penetration of said fastening means into said bone, the central portion and said stiffening portion will arch away from said bone to minimize damage thereto.

2. The fixation device set forth in claim 1 wherein said fastening means are generally wedge-shaped and are formed by inwardly bending the ends of said finger portions.

3. An internal fixation device for a bone fracture as claimed in claim 1, being made of surgical stainless steel or other suitable alloy, the stiffening structure comprising an elongate groove-like depression pressed in the metal.

* * * * *